(12) United States Patent
Firth et al.

(10) Patent No.: US 9,107,613 B2
(45) Date of Patent: Aug. 18, 2015

(54) HANDHELD SCANNING DEVICE

(75) Inventors: David G. Firth, Cle Elum, WA (US);
Brendan O. Beardsley, Ellensburg, WA (US); John P. Pella, Redmond, WA (US)

(73) Assignee: Provel, Inc., Cle Elum, WA (US)

( * ) Notice: Subject to any disclaimer, the term of this patent is extended or adjusted under 35 U.S.C. 154(b) by 692 days.

(21) Appl. No.: 13/469,294

(22) Filed: May 11, 2012

(65) Prior Publication Data
US 2013/0057652 A1    Mar. 7, 2013

Related U.S. Application Data

(60) Provisional application No. 61/531,406, filed on Sep. 6, 2011.

(51) Int. Cl.
| | |
|---|---|
| H04N 1/00 | (2006.01) |
| H04N 1/024 | (2006.01) |
| H04N 1/04 | (2006.01) |
| H04N 9/04 | (2006.01) |
| H04N 13/02 | (2006.01) |
| A61B 5/107 | (2006.01) |
| G01B 11/25 | (2006.01) |

(52) U.S. Cl.
CPC ............. *A61B 5/1077* (2013.01); *A61B 5/1079* (2013.01); *G01B 11/25* (2013.01); *A61B 2560/0425* (2013.01)

(58) Field of Classification Search
None
See application file for complete search history.

(56) References Cited

U.S. PATENT DOCUMENTS

| | | | | |
|---|---|---|---|---|
| 4,851,896 | A * | 7/1989 | Muranaga et al. | 358/443 |
| 5,521,366 | A * | 5/1996 | Wang et al. | 235/454 |
| 6,128,086 | A * | 10/2000 | Fowler et al. | 356/616 |
| 6,347,163 | B2 * | 2/2002 | Roustaei | 382/324 |
| 6,732,929 | B2 * | 5/2004 | Good et al. | 235/462.01 |
| 2004/0263117 | A1 * | 12/2004 | Kogan et al. | 320/114 |
| 2010/0117885 | A1 * | 5/2010 | Holbrook et al. | 342/22 |
| 2011/0075159 | A1 * | 3/2011 | Chang et al. | 356/625 |
| 2012/0092461 | A1 * | 4/2012 | Fisker et al. | 348/46 |

FOREIGN PATENT DOCUMENTS

WO   WO 2010145669   * 12/2010   ............. A61B 5/107

OTHER PUBLICATIONS http://www.artec3d.com/3d_scanners/comparative_table/; Artec 3D Scanners; Nov. 16, 2011.
http://www.noomeo.eu/; Noomeo; Nov. 16, 2011.
http://www.nikonmetrology.com/handheld_scanners/; Nikon; Nov. 16, 2011.
http://www.vialux.de/HTML/en_mobilc.htm; ViALUX; Nov. 16, 2011.

* cited by examiner

*Primary Examiner* — Beniyam Menberu
(74) *Attorney, Agent, or Firm* — Neustel Law Offices

(57) ABSTRACT

A handheld, cordless scanning device for the three-dimensional image capture of patient anatomy without the use of potentially hazardous lasers, optical reference targets for frame alignment, magnetic reference receivers, or the requirement that the scanning device be plugged in while scanning. The device generally includes a housing having a front end and a rear end. The rear end includes a handle and trigger. The front end includes a pattern projector for projecting a unique pattern onto a target object and a camera for capturing live video of the projected pattern as it is deformed around the object. The front end of the housing also includes a pair of focus beam generators and an indexing beam generator. By utilizing data collected with the present invention, patient anatomy such as anatomical features and residual limbs may be digitized to create accurate three-dimensional representations which may be utilized in combination with computer-aided-drafting programs.

3 Claims, 9 Drawing Sheets

HANDHELD SCANNING DEVICE

CROSS REFERENCE TO RELATED APPLICATIONS

I hereby claim benefit under Title 35, United States Code, Section 119(e) of U.S. provisional patent application Ser. No. 61/531,406 filed Sep. 6, 2011. The 61/531,406 application is currently pending. The 61/531,406 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a scanning device and more specifically it relates to a cordless handheld scanning device for the three-dimensional image capture of a target object such as patient anatomy without the use of potentially hazardous lasers, optical reference targets, magnetic reference receivers, or the requirement that the scanning device be plugged in while scanning.

2. Description of the Related Art

Any discussion of the related art throughout the specification should in no way be considered as an admission that such related art is widely known or forms part of common general knowledge in the field.

Structured light scanning has been in use for years to assist in capturing the shape of patient anatomy. Using structured light scanning, anatomical features and residual limbs can be digitized to create accurate three-dimensional representations. These representations may then be used with various CAD programs directed at various industries; such as the orthotics and prosthetics industries.

Existing structured light scanners suffer from a number of significant drawbacks. Generally, prior art scanners require the scanned object or the scanner to remain motionless while multiple pattern regressions are projected over the object. Movement of either the object or the scanner during such operations with prior art scanners can cause deleterious effects upon the finished three-dimensional model.

Additionally, existing structured light scanners often require the use of lasers which present the risk of causing ocular health hazards to live subjects. Further, the use of optical reference targets on the subject as is common with prior art scanners can be time consuming and wasteful for operators to apply. Magnetic reference receivers, which are also common in the field, are subject to inaccuracy due to nearby metallic objects or when used near magnetic resonance imaging (MRI) operations which are common within medical fields. Corded operation inhibits freedom of movement when scanning patients or objects.

Because of the inherent problems with the related art, there is a need for a new and improved cordless handheld scanning device for the three-dimensional image capture of a target object such as patient anatomy without the use of optical reference targets, magnetic reference receivers, potentially hazardous lasers, or a cord while scanning.

BRIEF SUMMARY OF THE INVENTION

The invention generally relates to a cordless handheld scanning device which includes a housing having a front end and a rear end. A handle and trigger are provided adjacent the rear end of the device. The front end of the housing includes a pattern projector for projecting a unique pattern onto a target object and a camera for capturing live video of the projected pattern as it is deformed around the object. The front end of the housing also includes a pair of focus beam generators for assisting in obtaining optimal positioning of the present invention during scanning operations. The front end of the housing may also include an indexing beam generator which is utilized by the video processing algorithm of the present invention to indicate a depth relationship from a datum plane established through a factory calibration process. By utilizing data collected with the present invention, patient anatomy such as anatomical features and residual limbs may be digitized to create accurate three-dimensional representations which may be utilized with computer-aided-drafting programs.

While the present invention is primarily directed toward the orthotics and prosthetics industries, it is appreciated that, because the scanner is capable of capturing three-dimensional shapes, it may also be utilized within other medical industries including but not limited to cosmetic, aesthetic and reconstructive surgery. Reverse engineering, virtual reality, entertainment production, cultural heritage and metrology applications are also foreseeable with the present invention.

There has thus been broadly outlined some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
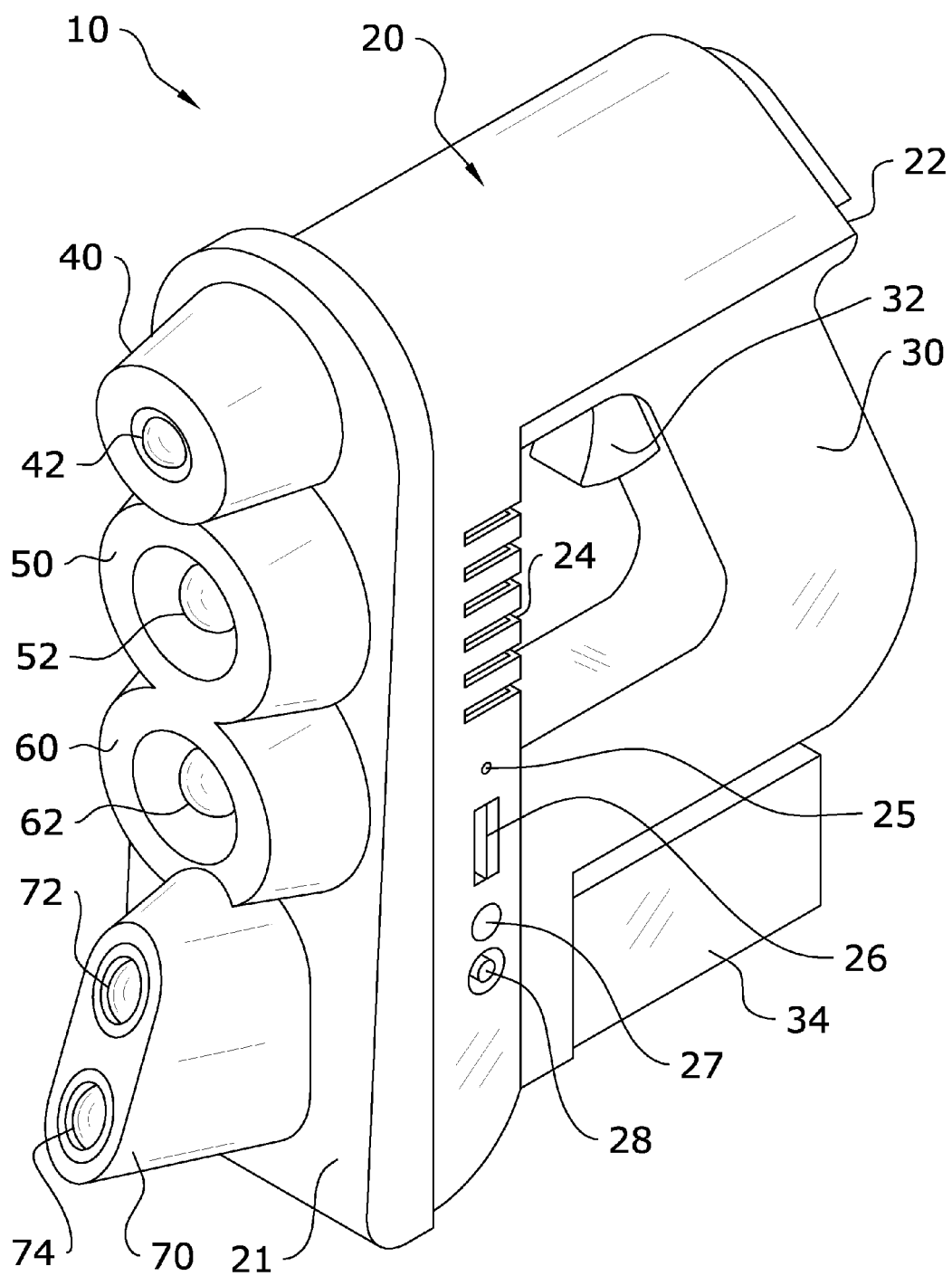
FIG. 1 is an upper perspective view of the present invention.

Turning now descriptively to the drawings, in which similar reference characters denote similar elements throughout the several views, FIGS. 1 through 6 illustrate a handheld scanning device 10, which comprises a housing 20 having a front end 21 and a rear end 22. A handle 30 and trigger 32 are provided adjacent the rear end 22 of the device 10. The front end 21 of the housing 20 includes a pattern projector 62 for projecting a unique pattern onto a target object and a camera 52 for capturing live video of the projected pattern as it is deformed around the object. The front end 21 of the housing 20 also includes a pair of focus beam generators 42, 74 for assisting in obtaining optimal positioning of the present invention during scanning operations. The front end 21 of the housing 20 may also include an indexing beam generator 72 which is utilized by the video processing algorithm of the present invention to indicate a depth relationship from a datum plane established through a factory calibration process. By utilizing data collected with the present invention, patient anatomy such as anatomical features and residual limbs may be digitized to create accurate three-dimensional representations which may be with computer-aided-drafting programs.

B. Housing

The handheld scanning device 10 will generally include a housing 20 which houses the various components of the present invention. The housing 20 will generally include a front end 21 which houses the various light projection and capture components of the present invention and a rear end 22 which includes a handle 30 and trigger 32. It is appreciated that various shapes and arrangements may be utilized for the housing 20 of the present invention, and its structure should not be construed as being limited to the exemplary structure shown in the figures.

The housing 20 will generally include venting 24 to assist with the cooling of the internal components thereof. The housing 20 may also include a reset button 25 for resetting the device 10 and a power button 27 for powering the device 10 on and off. An indicator light 28 may also be included for indicating whether the device 10 is powered on or off. The reset and power buttons 25, 27 may be positioned at various locations on the housing 20, but will preferably be located in a position which is easy to reach when gripping the present invention by its handle 30. Similarly, the indicator light 28 may be positioned at various locations on the housing 20, but will preferably be located in a position which is easily viewable when the present invention is in use.

The housing 20 will generally include a handle 30 extending from its rear end 22 as shown in FIG. 1. The handle 30 is comprised of a structure which may be gripped by an operator of the present invention when in use. In some embodiments, the handle 30 may be comprised of an ergonomic configuration. The handle 30 may also act as a conduit to support the trigger 32 of the present invention.

The trigger 32 of the present invention will be utilized to activate and deactivate the scanning device 10 when in use. The trigger 32 may be located at various positions on the handle 30 or housing 20, but will preferably be in a location which is easy to reach when holding the present invention by its handle 30. It is appreciated that the shape, positioning and orientation of the handle 30 and trigger 32 may vary in different embodiments and should not be construed as being limited by the exemplary configurations shown in the figures.

The housing 20 will also generally include a battery 34 which is utilized to power the various components of the scanning device 10. Various types and numbers of batteries 34 may be utilized. Further, the positioning of the battery 34 may vary, but will preferably be in a position which does not interfere with normal operation of the present invention as shown in FIG. 1, such as adjacent the rear end 22 of the housing 20.

Figure 8:
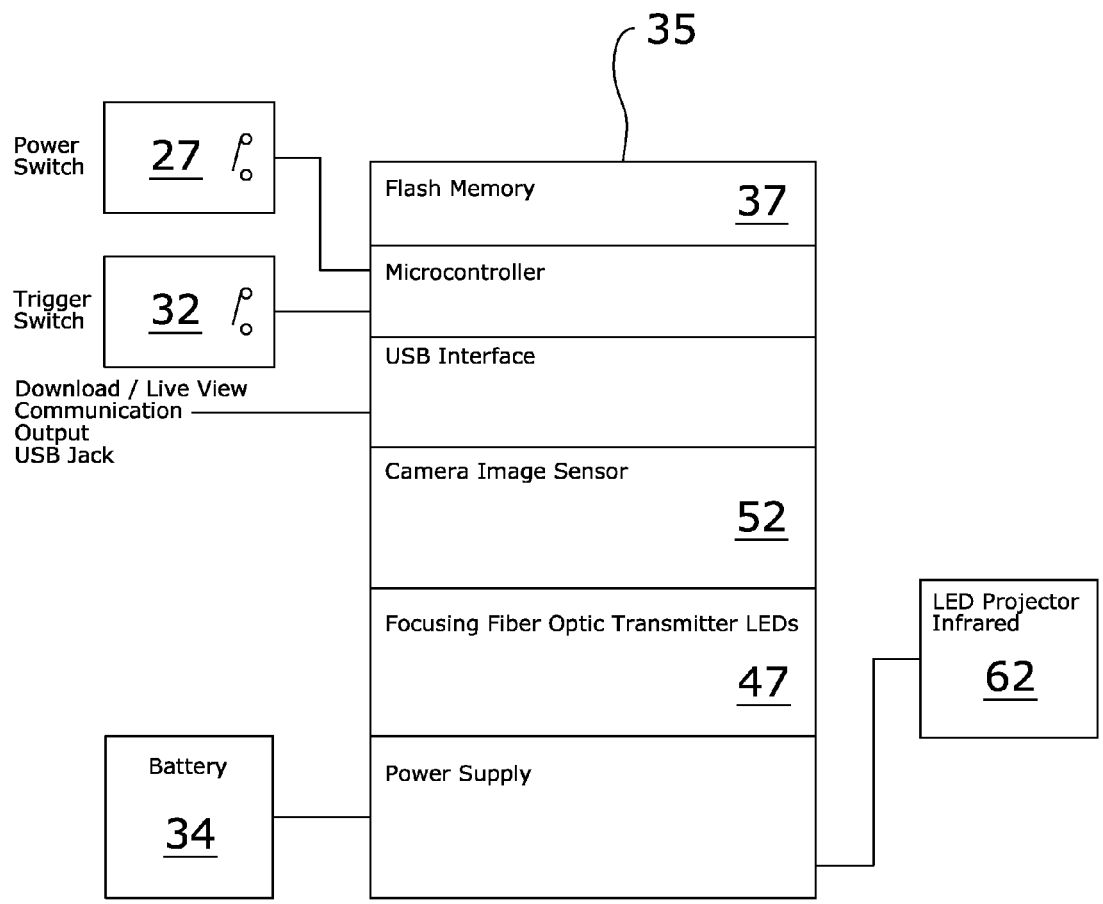
FIG. 8 is a block diagram illustrating the circuit board of the present invention.

The housing 20 will also generally store logic circuitry and internal memory. The logic circuitry, which is integrated into a circuit board 35 positioned within the housing 20, directs the operation of the various components of the present invention. As shown in FIG. 8, the circuit board 35 will generally include flash memory 37 for storing data captured by the present invention. Further, LED transmitters 47 will generally be positioned on the circuit board 35, and integrated with the beam generators 42, 72, 74. It is also appreciated that the circuit board 35 may include an accelerometer and gyroscope (not shown). Various types of accelerometers and gyroscopes may be utilized, though in a preferred embodiment the present invention will include a three-axis accelerometer and a three-axis gyroscope. Both the accelerometer and gyroscope are embedded on the circuit board 35 to allow movement and orientation sensing. Thus, the position of the scanner 10 may be calculated with each captured frame of image sensor data. The correlation of the image and spatial data helps to pre-align the 3D points that are later generated from the images. This pre-alignment greatly assists the speed and accuracy of the assembly of the scanned data.

Further, a data port 26 may be provided for transferring data from the device 10 to another device such as a computer as shown in FIG. 1. The data port 26 may be located at various positions on the housing and should not be construed as being limited to the positioning shown in the exemplary figures. Various types of data ports 26 may be utilized which allow the efficient transfer of data from the present invention to another computing device. In a preferred embodiment, a universal serial bus (USB) port 26 will be utilized.

Figure 2:
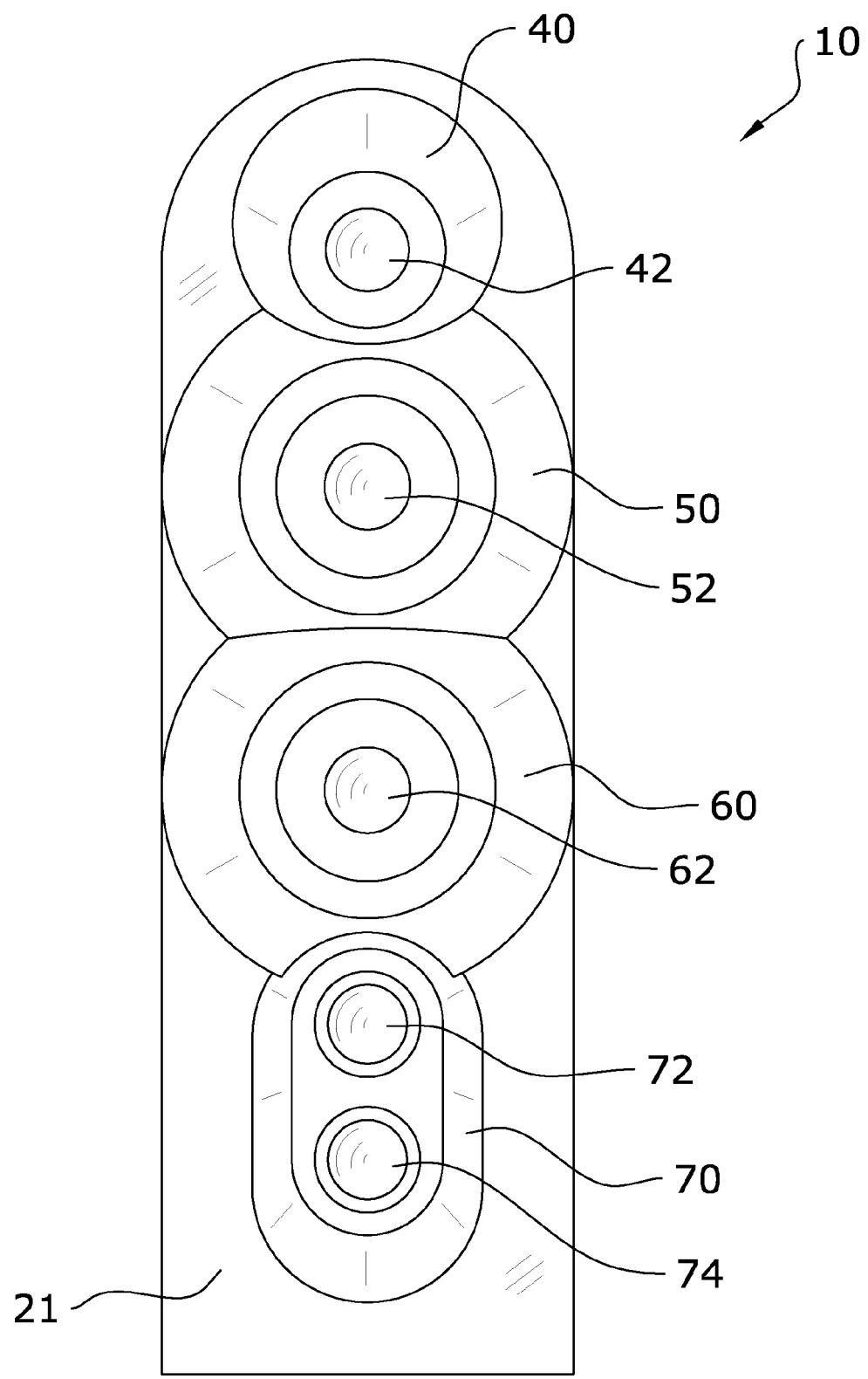
FIG. 2 is a front view of the present invention.

The front end 21 of the housing 20 will generally include the various scanning, projecting and image capturing components of the present invention. As shown in FIG. 2, the front end 21 of the housing 20 will generally include a first beam generator housing 40, a camera housing 50, a projector housing 60 and a second beam generator housing 70. These housings 40, 50, 60, 70 each store a component of the image projection, scanning and capture system which act in concert to capture the three-dimensional shape of an object.

Figure 3:
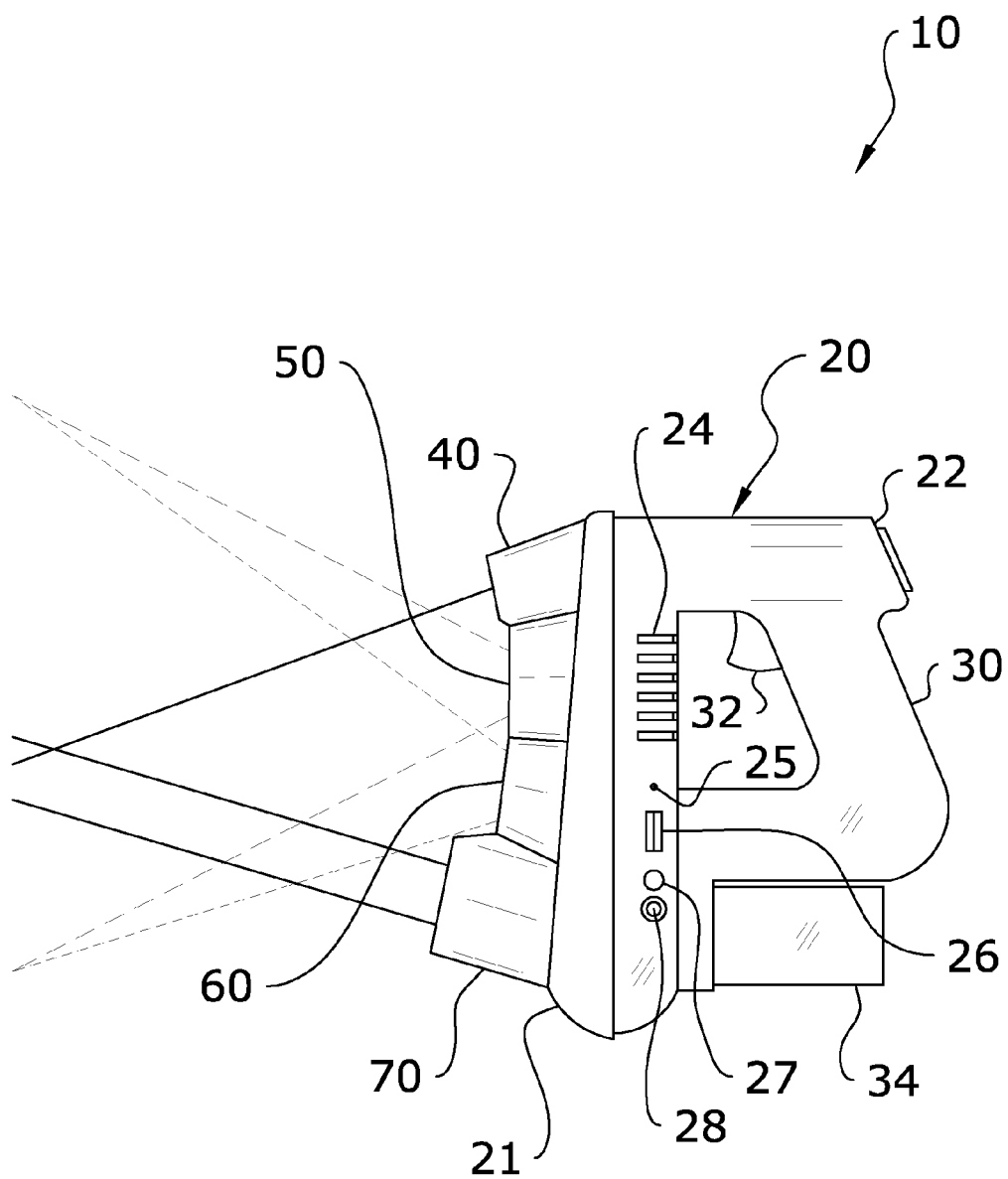
FIG. 3 is a side view of the present invention illustrating its optical fields of view.

A first beam generator housing 40 will generally be positioned adjacent the upper end of the front end 21 of the housing 20 as shown in FIG. 2. The first beam generator housing 40 will generally be positioned such that the beam generated from the first focus beam generator 42 extends diagonally downward in a manner which crosses the beam generated from the second focus beam generator 74 as shown in FIG. 3.

Figure 9:
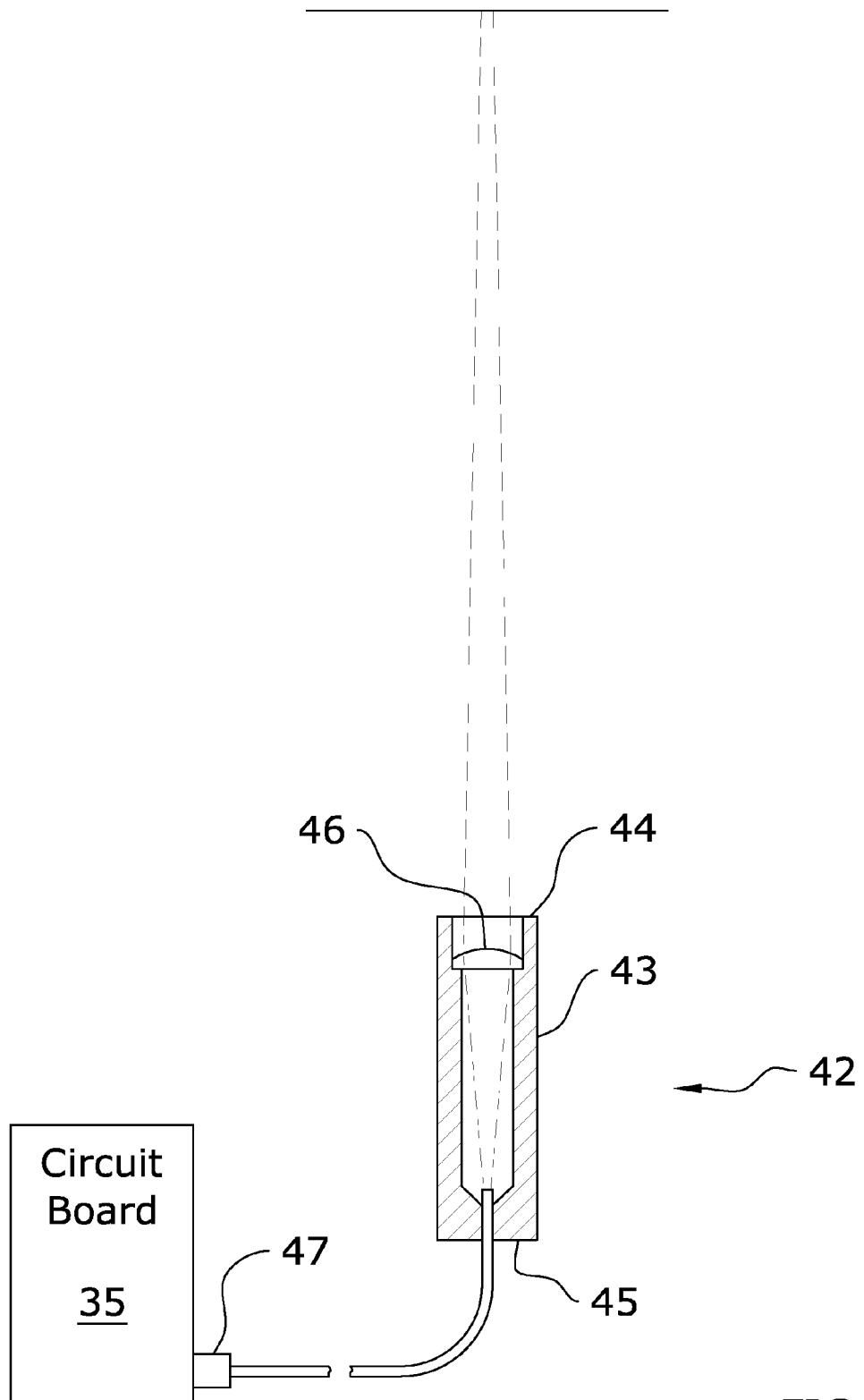
FIG. 9 is a top cutaway view of a beam generator of the present invention.

The first beam generator housing 40 houses the first focus beam generator 42 of the present invention. The first focus beam generator 42 is utilized in combination with the second focus beam generator 74 of the present invention to provide simultaneous depth range feedback to an operator of the present invention. Various types of beam generators may be utilized for the first focus beam generator 42 of the present invention, though it is appreciated that a preferred embodiment utilizes a first focus beam generator comprised of a lens housing 43 having a first end 44 and a second 45 as shown in FIG. 9.

A fiber optic conduit extends from an LED transmitter 47 positioned on the circuit board 35 to the first end 44 of the lens housing 43. The fiber optic conduit acts as collimator and point light source. A channel formed in the housing 43 adjacent its first end 44 guides the fiber optic to a position which transmits a light beam from the LED transmitter 47 through a lens 46 positioned adjacent the second end 45 of the lens housing 43. The lens 46 forms the transmitted light into a beam. Focus may be achieved by adjusting the axial location of the fiber optic conduit in the first end 44 of the lens housing 43. Various focal-length lenses 46 may be utilized with correspondingly dimensioned projection tube housings 43 to create different sized light dots at the specific target distance.

The camera housing 50 houses the camera 52 of the present invention. The camera housing 50 will preferably be positioned underneath the first beam generator housing 40 as shown in FIG. 1. The camera 52 is utilized to capture live video of the projected pattern from the pattern projector 62 interacting with the target object. The camera 52 will preferably be configured to capture the entirety of the projected pattern as shown in FIG. 3. Various types of cameras 52 may be utilized, so long as the camera 52 is adapted to capture live video in real-time in a format which is compatible with the other components of the present invention. It is also appreciated that, in some embodiments of the present invention, multiple cameras 52 may be utilized. By way of example and without limitation, additional camera(s) 52 may be utilized to pick up texture/color images.

The projector housing 60 houses the pattern projector 62 of the present invention. The projector housing 60 will preferably be positioned underneath the camera housing 50 as shown in FIG. 1. However, it is appreciated that, in some embodiments, the positioning of the camera housing 50 and projector housing 60 may be reversed. The pattern projector 62 is utilized to cast a single pattern of structured light upon the target object. Various types of pattern projectors 62 may be utilized with the present invention. In a preferred embodiment, an infrared projector 62 will be utilized. The pattern is captured by the camera 52 of the present invention and processed for image scanning and capture.

Figure 6:
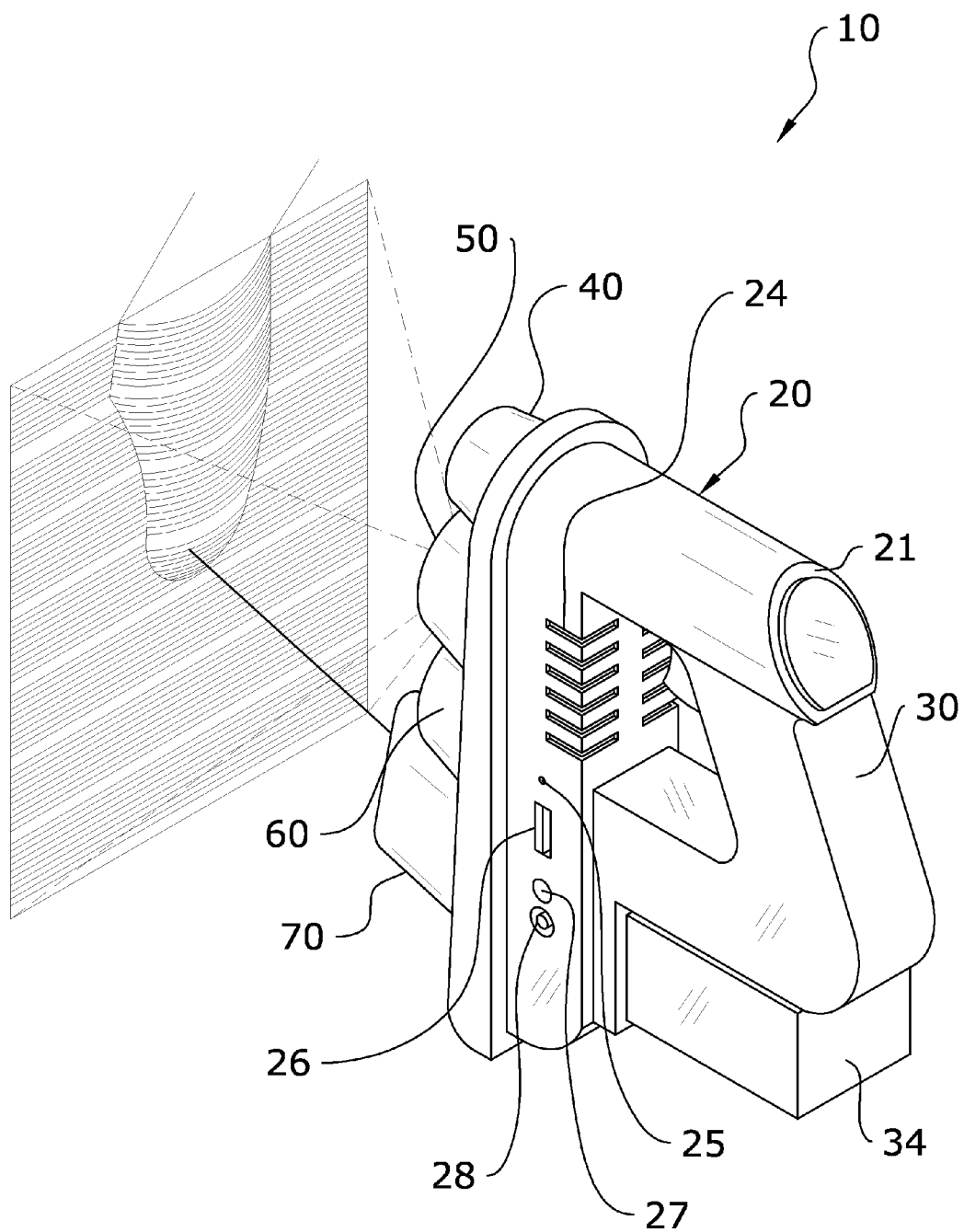
FIG. 6 is an upper perspective view illustrating the projected pattern and indexing beam as they contour around a target shape.
Figure 7:
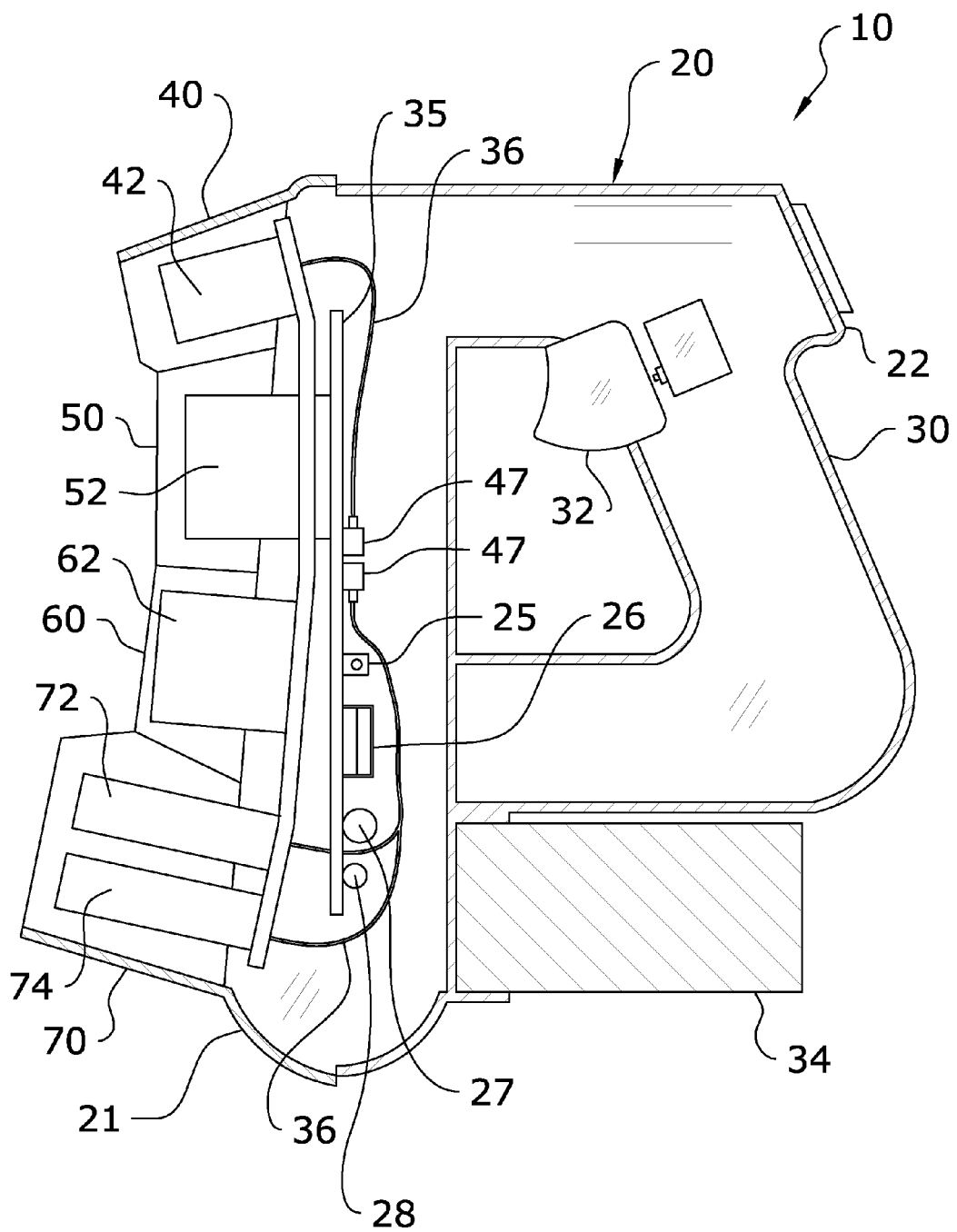
FIG. 7 is a side sectional view of the present invention.

The pattern projected by the pattern projector 62 of the present invention is unique in that it utilizes minor (I-stripe) and major (Key stripe) lines to aid the processes of image indexing, scale establishment and location identification. The projected pattern may include an equal number of minor lines between equally spaced major lines as shown in FIG. 6, or it may consist of varying numbers of minor lines between major lines as an additional locational aid to the image processing operations.

The second beam generator housing 70 houses both the indexing beam generator 72 and second focus beam generator 74 of the present invention. The second beam generator housing 70 is preferably positioned beneath the projector housing 60 on the front end 21 of the housing 20 as shown in FIG. 2. Generally, the second beam generator housing 70 will be configured to direct the beams generated from the indexing beam generator 72 and second focus beam generator 72 in an upward diagonal direction as shown in FIG. 3.

The indexing beam generator 72 is comprised of a generator which directs a single beam to a central location in the plane of projection of the present invention. The indexing beam generator 72 is generally positioned within the second beam generator housing 70 at a position which is directly above the second focus beam generator 74 of the present invention, though other configurations may be utilized. The index dot generated by the indexing beam generator 72 is utilized by the video processing algorithm of the present invention to indicate a depth relationship from a datum plane established through a factory calibration process.

The present invention utilizes the dot projected by the indexing beam generator 72 to assist in determining image data validity prior to mesh extraction. The projection of the indexing beam directly corresponds to surface location being respectively closer or further from the scanner 10 than the datum plane where focus beam points from the first and second focus beam generators 42, 74 converge. If the positive vertical dot offset is too large, it is inferred that the cell offset is greater than the maximum discriminable offset. Thus, the cells are too displaced to determine their index by comparison to the baseline. This situation will occur when the scanner is held too far away from the target object. If the indexing dot is not found at all, the image is discharged and mesh extraction is aborted for that frame. This occurs when the scanner 10 is too close to the target or the target is not scannable due to a surface's reflective qualities.

The second focus beam generator 74 is utilized in combination with the first focus beam generator 42 of the present invention to provide simultaneous depth range feedback to an operator of the present invention. The convergence of the respective focus beams from the first and second focus beam generators 42, 74 indicates the optimal range to position the housing 20 from the object being scanned and provides a cue for aiming the device 10.

It is appreciated that both the indexing beam generator 72 and the second focus beam generator 74 are preferably comprised of the same structure as the first focus beam generator 74; utilizing the lens 46 and housing 43 in combination with an LED transmitter 47 to generate points of light without the need for lasers as described previously with respect to the first focus beam generator 42.

C. Operation of Preferred Embodiment

In use, an operator of the present invention first powers up the device 10 utilizing the power button 27. The device 10 may be held in the hands of the operator using its handle 30 and pointed at a target object. To begin image capturing, the trigger 32 is depressed which activates the pattern projector 62, camera 52 and beam generators 42, 72, 74 of the present invention.

Figure 4:
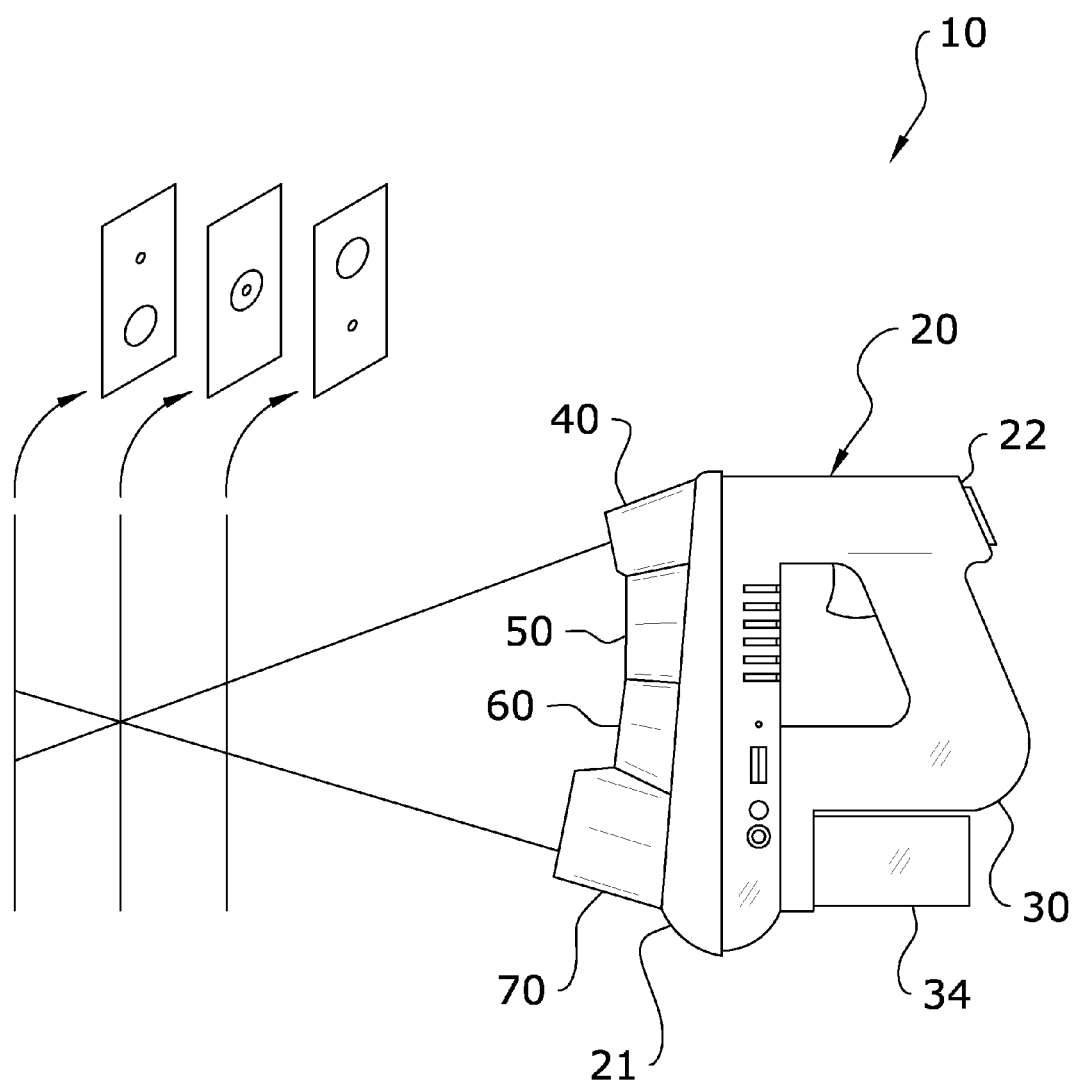
FIG. 4 is a side view of the present invention illustrating the effect of standoff distance on focus beam convergence.

The positioning of the respective beams generated by the focus beam generators 42, 74 may be utilized to determine the optimal range for positioning of the present invention with respect to the object. As illustrated in FIG. 4, the respective beams generated by the focus beam generators 42, 74 will converge to a single point when the present invention is an optimal distance from the object being scanned.

Figure 5:
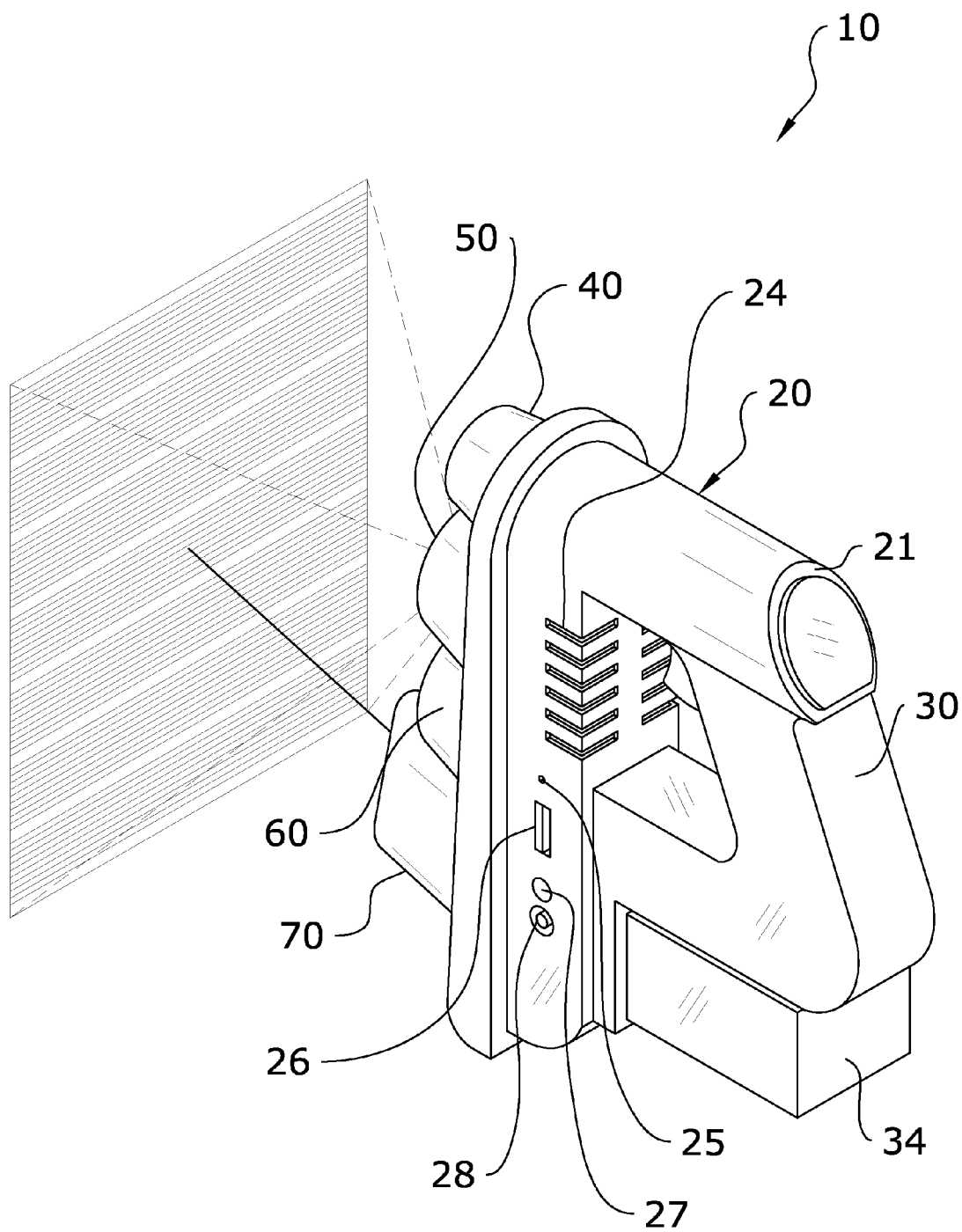
FIG. 5 is an upper perspective view illustrating the projected pattern and indexing beam of the present invention.

With the device 10 positioned at an optimal distance, the pattern projector 62 focuses a single pattern of structured light upon the target object as shown in FIG. 5. The camera 52 simultaneously captures live video of the pattern interacting with the target object. The video captured by the camera 52 is stored in memory (not shown) within the scanning device 10 and may later be transferred via cable (i.e. through use of the data port 26) or wirelessly to a host computing device. The host computing device utilizes a set of algorithms to compare the stream of video frame images to a set of datum images. This comparison generates a large set of oriented points which may be connected to present surface elements of the scanned target object. Various standard computer file types, including but not limited to AOP, OBJ and STL formats, may thus be generated and exported for use in a variety of CAD software packages.

The novel algorithm of the host computing device assembles multiple processed frames together to form a digitalization of the scanned object. Structured, infrared light is projected upon the target object by the pattern projector 62 and captured by the camera 52. The use of infrared light projection provides increased immunity to errors caused by ambient light and improves the ability to pick up all skin tones equally. The dark-light borders of the projected pattern are converted to a set of points with unique spatial locations. The image is preferably comprised of a 10 bit gray-scale packed image and the pattern stripe boundaries are detected using a one-dimensional Gaussian, zero-crossing method.

Boundary points are collected for each perpendicular scan line. Boundary distance confidence levels are calculated to discriminate true stripe pattern edges from false pattern edges. Boundaries are grouped into cells which correlate to the key stripes and interstitial I-stripes. Cell indexes are identified by comparing to cell locations in previously obtained, baseline datasets which represent the zero depth plane. The zero depth plane coincides with the datum plane.

A two-dimensional image to three-dimensional view transformation is performed as part of the algorithm. Each boundary point in a scan line has a unique location point which may be characterized from vectors. Because the points are computed in ordered rows as scan lines, row and position numbers are used to determine triangle indices. The collection may then be saved out as a standard triangle description file (i.e. OBJ type), or various other types of files.

Because the scanner 10 acquires images quickly, the amount of offset between meshes can be small. A variation of the known iterated closest point (ICP) algorithm is used to align successive meshes. ICP successively translates and rotates meshes closer to each other to achieve optimal correspondence and alignment. For the necessary pre-alignment, each successive mesh inherits the transform of the previous mesh as its starting point. The orientation assistance provided by this technique effectively pre-positions meshes in space prior to the ICP process.

When loaded, the vertices that are closer to the centroid of the vertices are flagged in a hash table. When closest squared distances are calculated, only the centermost points in the target mesh are aligned. This method minimizes and usually eliminates vertices which fall outside the edge of the source mesh, which reduces the common ICP problems of travel or sliding. After each mesh is aligned to its predecessor, the final mesh is aligned back to the first. Then a looping alignment is performed to reduce drift that may occur due to sensitive dependence on initial meshes. This process may also be supervised by permitting the user to hand-align one mesh to another while watching a real-time onscreen value.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A handheld, cordless scanning device for the three-dimensional shape capture of a target object, comprising:
    a housing, wherein said housing includes a front end and a rear end, wherein said housing further includes a power button, reset button and indicator light, wherein said housing further includes a data port;
    a handle positioned adjacent said rear end of said housing, wherein said handle includes a trigger;
    a circuit board positioned within said housing, wherein said circuit board includes an accelerometer and a gyroscope;
    flash memory for storing data positioned within said housing;
    a first LED transmitter connected to said circuit board;
    a first focus beam generator positioned on said front end of said housing adjacent an upper end of said housing, wherein said first focus beam generator is comprised of a lens housing and a lens, wherein said lens housing is connected to said first LED transmitter by a first fiber optic conduit;
    a second LED transmitter connected to said circuit board;
    a second focus beam generator positioned on said front end of said housing adjacent a lower end of said housing, wherein said second focus beam generator is comprised of a lens housing and a lens, wherein said lens housing is connected to said second LED transmitter by a second fiber optic conduit;
    an indexing beam generator positioned on said front end of said housing, wherein said indexing beam generator is comprised of a lens housing and a lens, wherein said lens housing is connected to said second LED transmitter by said second fiber optic conduit, wherein said indexing beam generator projects an indexing dot onto said target object;
    a video capture device positioned on said front end of said housing; and
    a pattern projection device positioned on said front end of said housing;
    wherein a first beam generated by said first focus beam generator extends diagonally downward and wherein a second beam generated by said second focus beam generator extends diagonally upward, wherein said first beam and said second beam cross at an optimal position for said target object to be placed.

2. The handheld scanning device for the three-dimensional shape capture of a target object of claim 1, wherein said pattern projection device is comprised of an infrared projector.

3. The handheld scanning device for the three-dimensional shape capture of a target object of claim 2, wherein said housing further includes a removable battery.

* * * * *